United States Patent [19]

Jackson

[11] Patent Number: 5,360,937
[45] Date of Patent: Nov. 1, 1994

[54] 1,3-CYCLOBUTANEDIONE-BISKETALS, PROCESS FOR THEIR PRODUCTION AND THEIR USE

[75] Inventor: Barry Jackson, Brig-Glis, Switzerland

[73] Assignee: Lonza Ltd., Gampel/Valais, Switzerland

[21] Appl. No.: 35,089

[22] Filed: Mar. 22, 1993

[30] Foreign Application Priority Data

Mar. 24, 1992 [CH] Switzerland ............... 929/92

[51] Int. Cl.⁵ ............................................. C07C 45/43
[52] U.S. Cl. ...................................... 568/348; 568/361
[58] Field of Search ............................ 568/361, 348

[56] References Cited

U.S. PATENT DOCUMENTS

| 3,129,248 | 4/1964 | England | 568/361 |
|---|---|---|---|
| 3,402,181 | 9/1968 | Erickson et al. | 568/361 |
| 5,087,756 | 2/1992 | Jackson et al. | 564/457 |
| 5,118,847 | 6/1992 | Jackson et al. | 564/281 |
| 5,118,861 | 6/1992 | Jackson et al. | 568/347 |
| 5,130,492 | 7/1992 | Scholl et al. | 568/348 |

FOREIGN PATENT DOCUMENTS

| 442431 | 8/1991 | European Pat. Off. | 568/348 |
|---|---|---|---|
| 444563 | 9/1991 | European Pat. Off. | 568/348 |
| 1140207 | 1/1969 | United Kingdom | 568/348 |

OTHER PUBLICATIONS

Hagemann et al., "Methoden der Organishchen Chemie, Houben–Weyl", vol. E 14a/1, (1991), p. 280.

*Primary Examiner*—James H. Reamer
*Attorney, Agent, or Firm*—Fisher, Christen & Sabol

[57] ABSTRACT

Bisketals of 1,3-cyclobutanedione with monovalent and divalent alcohols as well as processes for their production from 1,3-cyclobutanedione or from 3-acetoxy-2-cyclobuten-1-one contained in the distillation residues of the diketene production. The bisketals are suitable intermediate products for the production of squaric acid, for the production and/or purification of 1,3-cyclobutanedione, or as a stable form for storage or substitute for this unstable dione.

13 Claims, No Drawings

1,3-CYCLOBUTANEDIONE-BISKETALS, PROCESS FOR THEIR PRODUCTION AND THEIR USE

BACKGROUND OF THE INVENTION

1. Field Of The Invention

The invention relates to new 1,3-cyclobutanedione-bisketals as well as processes for their production and for their use, especially for the production of squaric acid.

2. Background Art

Squaric acid (1,2-dihydroxycyclobutene-3,4-dione) is a useful intermediate product for the production of dyes, herbicides and pharmaceutically active ingredients. For a long time no economical production process for squaric acid was known, it has been possible in the meantime to produce squaric acid from 3-acetoxy-2-cyclobuten-1-one ("triketene") or from 1,3-cyclobutanedione or the enolates obtainable from it (European Published Patent Application Nos. 442431 and 444563). However, these processes generally require an expensive isolation of the triketene or of the 1,3-cyclobutanedione having little stability.

DESCRIPTION OF THE INVENTION

The main objective of the invention is to provide stable derivatives of 1,3-cyclobutanedione, which can also be easily produced and isolated from the triketene-containing residue resulting in large amounts in the industrial production of diketene from ketene, as well as to indicate their reaction to squaric acid. Other objectives and advantages of the invention are set out herein or obvious herefrom to one skilled in the art.

The objectives and advantages of the invention are achieved by the processes and compounds of the invention.

The 1,3-cyclobutanedione-bisketals according to the invention have the general formula:

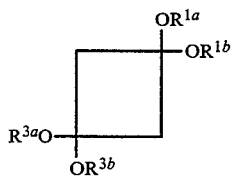
  I wherein either $R^{1a}$, $R^{1b}$, $R^{3a}$ and $R^{3b}$ are the same and respectively each represents a linear or branched lower alkyl group, or respectively $R^{1a}$ and $R^{1b}$ as well as $R^{3a}$ and $R^{3b}$ together are the same and with the ketal-oxygen atoms and the intermediate carbon atom respectively form a five-membered or six-membered spiro-linked ring with the cyclobutane ring optionally substituted by one or more lower alkyl groups.

Thus, the bisketals of 1,3-cyclobutanedione with monovalent alcohols correspond to the first alternative, and those with 1,2-diols or 1,3-diols to the second alternative. Lower alkyl groups are to be understood here and in the following to be alkyl groups with 1 to 6, preferably 1 to 4 carbon atoms, for example, methyl, ethyl, propyl, isopropyl, butyl, isobutyl, sec-butyl, pentyl, isopentyl and hexyl. Especially preferred are the bisketals that are derived from methanol or ethanol, in which the lower alkyl groups thus are methyl or ethyl. The bisketals with 1,2-diols and 1,3-diols which are preferred are those in which $R^{1a}$ and $R^{1b}$ as well as $R^{3a}$ and $R^{3b}$ together each form a 1,2-ethanediyl, 1,2-propanediyl, 1,3-propanediyl, 1,2-butanediyl, 1,3-butanediyl, 2,3-butanediyl, 2,2-dimethyl-1,2-propanediyl or 2,3-dimethyl-2,3-butanediyl group, i.e., are derived from ethanediol, 1,2-propanediol, 1,3-propanediol, 1,2-butanediol, 1,3-butanediol, 2,3-butanediol, 2,2-dimethyl-1,3-propanediol (neopentylglycol) or 2,3-dimethyl-2,3-butanediol (pinacol).

The bisketals according to the invention can be produced, for example, from 1,3-cyclobutanedione by reaction with the corresponding orthoformic ester in the presence of an acid catalyst. The orthoformic esters necessary for this purpose have the general formula:

  II wherein $R^a$ and $R^b$ have the meanings mentioned above in formula I for $R^{1a}$ and $R^{1b}$ as well as $R^{3a}$ and $R^{3b}$, and R is a lower alkyl group. If $R^a$ and $R^b$ are also lower alkyl groups, i.e., if a trialkylorthoformate is involved, thus in addition R, $R^a$ and $R^b$ are the same. The preferred orthoformic esters result from the preferably to be produced bisketals I, so especially preferred are thus trimethylorthoformate and triethylorthoformate. Correspondingly, the corresponding spiro ketals can be produced from cyclic orthoformic esters, in which $R^a$ and $R^b$ together with the directly bound oxygen atoms and the intermediate formate-carbon atoms form a five-membered or six-membered ring optionally substituted by one or more lower alkyl groups. An example for such an orthoformic ester is 2-methoxy-1,3-dioxolane, the mixed orthoformate of ethanediol and methanol.

If the reaction is performed with a trialkylorthoformate, so that $R=R^a=R^b$ applies, then the reaction is preferably performed in the presence of the corresponding alcohol ROH, which at the same time optionally acts as a solvent.

As the acid catalyst preferably acid cation exchangers, for example Amberlyst®-15, are used. The reaction of the 1,3-cyclobutanedione with the orthoformic ester is suitably performed at a temperature of −10° to +40° C., preferably 0° to 20° C. In this case the orthoformic ester is advantageously used in an amount of 2 to 10 mol, relative to 1 mole of the 1,3-cyclobutanedione.

The bisketals according to the invention are thermally stable and can be easily separated and/or purified by distillation under reduced pressure.

A further process according to the invention for the production of bisketals according to the invention, especially those which are derived from 1,2- or 1,3-diols, comprises two steps, in which in the above-described way 1,3-cyclobutanedione is first reacted with a trialkylorthoformate of the general formula:

$$HC(OR)_3 \qquad III$$

wherein R is a lower alkyl group, to the corresponding bisketal of the general formula:

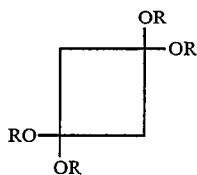

and then is converted with a diol of the general formula:

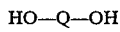

wherein Q is an ethanediyl or propanediyl group, optionally substituted by one or more lower alkyl groups, in a reketalization into the corresponding spiroketal. According to this process the bis-dimethyl ketal or bis-diethyl ketal preferably is first produced with trimethyl or triethyl orthoformate. Group Q is preferably 1,2-ethanediyl, 1,2-propanediyl, 1,3-propanediyl, 1,2-butanediyl, 2,3-butanediyl, 2,2-dimethyl-2,3-propanediyl or 2,3-dimethyl-2,3-butanediyl.

A still further process according to the invention for the production of the bisketals according to the invention starts from 3-acetoxy-2-cyclobuten-1-one (triketene) of the formula:

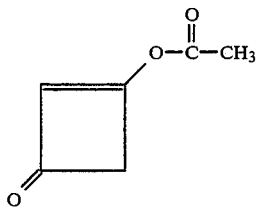

In this case the monoenolacetate of 1,3-cyclobutanedione is involved. For this purpose suitably the triketene is reacted in the way described above for 1,3-cyclobutanedione with an orthoformic ester. Thus, advantageously, instead of pure triketene, the triketene-containing residue of the industrial diketene distillation is used. In particular with the especially preferred use of trimethylorthoformate as the orthoformic ester the triketene can be removed in this way almost quantitatively from the residue and used. Thus, the isolation of the bisketal can take place by means of a simple distillation under reduced pressure, for example in a thin-layer evaporator.

A preferred use of the 1,3-cyclobutanedione-bisketals according to the invention is the initial product for the production of squaric acid. In this case the ketals are first halogenated and then the halogen compounds formed as intermediate product are hydrolyzed.

The halogenation is advantageously performed in the presence of water or after addition of water. Presumably the ketal functions are totally or partially hydrolyzed in the process and the hydrolysis products are halogenated in situ.

Preferably the halogenation is performed with elementary chlorine or bromine, especially preferred with bromine. Thus, the halogen is suitably used in an amount of 2.5 to 4 mol, preferably 3 to 3.5 mol, per mol of initial material. The halogenation is suitably performed at a temperature of 0° to 80° C., preferably of 10° to 40° C. As the solvent all protic and aprotic solvents resistant to elementary halogen are suitable, especially lower aliphatic carboxylic acids, their esters and anhydrides, as well as halogenated alkanes. As examples of these solvents are mentioned acetic acid, ethyl acetate, acetic anhydride, dichloromethane, trichloromethane and tetrachloromethane. Acetic acid is especially preferred as the solvent.

The hydrolysis to the squaric acid is preferably performed with sulfuric acid, which contains the necessary amount of water (2 mol for 1 mol of squaric acid) or an excess of water. The hydrolysis can be performed with water alone or with other aqueous acids. Examples of acids are mineral acids, such as, hydrochloric acid, hydrobromic acid and aqueous phosphoric acid, strong carboxylic acids, such as, aqueous formic acid and aqueous trifluoroacetic acid, and aqueous sulfonic acids, such as, methane sulfonic acid and p-toluene sulfonic acid. The hydrolysis is suitably performed at a temperature of 50° to 150° C., preferably at 80° to 120° C.

Another preferred use of the 1,3-cyclobutanedione-bisketals according to the invention is the production and/or purification of 1,3-cyclobutanedione. For this purpose the bisketals are hydrolyzed in the presence of an acid. This use is especially of interest for the production of 1,3-cyclobutanedione from the triketene-containing diketene distillation residue, since the isolation and purification of the triketene can be avoided in this way. Because of its easy convertibility into 1,3-cyclobutanedione and its stability the bisketals according to the invention are suitable quite generally as a form of storage of the unstable 1,3-cyclobutanedione.

The following examples illustrate the embodiment of the invention.

EXAMPLE 1

1,1,3,3-Tetramethoxycyclobutane from 1,3-cyclobutanedione 3.12 g of 1,3-cyclobutanedione (content 94.2 percent, 33 mmol) was dissolved in 25 ml of methanol and cooled to 0° C. The solution was mixed with 0.78 g of Amberlyst®-15 and then within 20 minutes mixed by instillation with 37.9 g of trimethylorthoformate (98 percent, 350 mmol). After 16 hours of more stirring at 0° C. the catalyst was filtered off and the filtrate was concentrated by evaporation at 30° C./15 mbar. The residue (5.9 g) was distilled in a bulb tube apparatus at 55°–65° C./0.8 mbar. The yield of product was 4.79 g, with a content (GC) of 98.4 percent, which corresponds to 76.4 percent of theory. Other data concerning the product is:

$^1$H-NMR: (CDCl$_3$, 300 MHz) δ 3.19 (s, 12H), 2.34 (s, 4H)

MS: m/z(%): 161(8, M—15), 145(11), 113(8), 88(50), 71(5), 5S(31), 43(100).

EXAMPLE 2

1,1,3,3-Tetraethoxycyclobutane from 1,3-cyclobutanedione 3.12 g of 1,3-cyclobutanedione (content 94.2 percent, 35 mmol) was dissolved in 25 ml of ethanol and stirred 24 hours at room temperature with 0.78 g of Amberlyst®-15 and 52.9 g of triethylorthoformate (98 percent, 350 mmol). Then the catalyst was filtered off and the filtrate concentrated by evaporation at 20° C./0.2 mbar. The residue (8.1 g) was distilled in a bulb tube apparatus at 60°–70° C./0.15 mbar. The yield of product was 7.22 g, with a content (GC) of 94.7 percent, which corresponds to 84.1 percent of theory. Other data concerning the product is:

¹H-NMR: (CDCl₃, 300 MHz) δ 3.44 (q, 8H), 2.38 (s, 4H), 1.21 (t, 12H)

MS: m/z(%): 203(5, M-29), 187(5), 129(11), 116(15), 101(8), 89(28), 85(27), 60(25), 43(100).

EXAMPLE 3

1,1,3,3-Tetrabutoxycyclobutane from 1,3-cyclobutanedione 1.77 g of 1,3-cyclobutanedione (content 95.0 percent, 20 mmol) was dissolved in 15 ml of butanol and stirred 7 hours at 25° C. with 0.44 g of Amberlyst ®-15 and 10.33 g of tributylorthoformate (99 percent, 44 mmol). Then the catalyst was filtered off and the filtrate concentrated by evaporation at 50° C./15 mbar. The residue (7.7 g) was distilled in a bulb tube apparatus at 120°–135° C./0.03 mbar. The yield of product was 3.87 g, with a content (GC) of 97.0 percent, which corresponds to 54.5 percent of theory. Other data concerning the product is:

¹H-NMR: (CDCl₃, 300 MHz) δ 3.35 (t, 8H), 2.34 (s, 4H), 1.54 (m, sH), 1.49 (m, 8H), 0.93 (t, 12H).

MS: m/z(%): 287(9, M-57), 271(17), 231(10), 215(1), 175(2), 157(54), 117(40), 103(60), 101(65), 85(22), 61(100), 56(64), 43(23), 41(59).

EXAMPLE 4

1,1,3,3-Tetramethoxycyclobutane from the Diketene Distillation Residue 250 g of diketene residue with a content of 52.5 g (0.416 mol) of 3-acetoxy-2-cyclobuten-1-one (triketene) and 15.0 g (0.178 mol) of diketene were dissolved in 250 g of methanol and cooled to 0° C. Then 12.49 g of Amberlyst ®-15 and 113.7 g of trimethylorthoformate (98 percent, 1.05 mol) were added and the mixture was stirred 20 hours at 10° C. The catalyst was filtered off and the filtrate concentrated by evaporation at 20° C./5 mbar. The residue (235.7 g) was distilled in a SAMBAY thin-layer evaporator at 100° C./1–2 mbar. The yield of product was 89.9 g, with a content (GC) of 77.1 percent, which corresponds to 94.6 percent of theory, relative to the 3-acetoxy-2-cyclobuten-1-one in the starting material.

EXAMPLE 5

1,4,8,11-Tetraoxadispiro[4.1.4.1]dodecane 4.56 g of 1,1,3,3-tetramethoxycyclobutane (content 96.7 percent, 25 mmol) in 19.7 g of ethanediol was heated to 135° C. Thus, first the main separation of the resulting methanol at normal pressure and then (after 2 hours) the rest of the readily volatile components were distilled off at 200 mbar. The product crystallized out from the residue during cooling to room temperature and was filtered off and dried at 20° C./0,005 mbar. The yield of product was 2.11 g, with a content (GC) of 82.8 percent, which corresponds to 40.6 percent of theory. Other data concerning the product is:

Melting point: 95°–103° C.

¹H-NMR: (CDCl₃, 300 MHz) δ 3.93 (s, 8H), 2.69 (s, 4H)

MS: m/z(%): 173(0.1, M+1), 141(2), 112(3), 100(23), 86(100), 68(7), 56(3), 55(4), 42(94).

EXAMPLE 6

1,5,9,13-Tetraoxadispiro[5.1.5.1]tetradecane 4.56 g of 1,1,3,3-tetramethoxycyclobutane (content 96.7 percent, 25 mmol) in 23.5 g of 1,3-propanediol was heated to 140° C. The resulting methanol was distilled off within 6 hours at 100 mbar and the reaction mixture was then cooled to room temperature, and the product recrystallized. The crystals were filtered off and dried at 70° C./0.02 mbar. The yield of the product was 2.10 g, with a content (GC) of 87.4 percent, which corresponds to 36.6 percent of theory. Other data concerning the product is:

Melting point: 147°–151° C.

¹H-NMR: (CDCl₃, 300 MHz) δ 3.86 (t, 8H), 2.53 (s, 4H) 1.7 (quint, 4H).

MS: m/z(%): 201(0.5, M+1), 172(2), 157(6), 140(1), 113(25), 100(100), 72(18), 70(14), 57(9), 42(75).

EXAMPLE 7

3,3-11,11-Tetramethyl-1,5,9,13-tetraoxadispiro[5.1.5.1-]tetradecane 31.88 g of 2,2-dimethyl-1,3-propanediol was heated to 140° C. with 4.56 g of 1,1,3,3-tetramethoxycyclobutane (content 96.7 percent, 25 mmol). The resulting methanol was distilled off at mbar within 2 hours. Then the excess diol was removed in a sublimator at 140° C./50 mbar, and the product remained as residue. The yield of product was 3.95 g, with a content (GC) of 93.5 percent, which corresponds to 52.4 percent of theory. Other data concerning the product is:

Melting point: 166°–171° C.

¹H-NMR: (CDCl₃, 300 MHz) δ 3.44 (s, 8H), 2.52 (s, 4H) 0.98 (s, 12H)

MS: m/z(%): 257 (1, M+1), 241(5), 200(2), 186(5), 171(2), 141(32), 128(100), 86(11), 85(11), 69(90), 57(38), 55(32), 43(49), 42(36), 41(70).

EXAMPLE 8

Squaric acid 104.6 g of 1,1,3,3-tetramethoxycyclobutane (content 85.9 percent, 0.50 mol) was dissolved in 1000 ml of acetic acid with 36.6 g of water. The solution was mixed with 4.07 g (50 mmol) of hydrobromic acid in 8.2 g of acetic acid and stirred 30 minutes at 10° C. Then 284.4 g (1.78 mol) of bromine was instilled within 1.5 hours and the mixture was stirred for another 1.25 hours at 15° C. The reaction mixture was concentrated by evaporation at 40° C./15 mbar to 300 ml and was instilled at 100° C. within 1.5 hours in a mixture of 250 ml of sulfuric acid and 18.0 g (1 mol) of water and a vigorous gas generation (HBr) took place and a suspension was formed. The latter was stirred for another 13 hours at 100° C., cooled and filtered. The filter cake was washed three times each with 100 ml of acetone and then dried at 20° C./0.1 mbar. The yield of product was 51.46 g, with a content (HPLC) of 93.3 percent, which corresponds to to 84.2 percent of theory.

EXAMPLE 9

1,3-Cyclobutanedione 1.82 g of 1,1,3,3-tetramethoxycyclobutane (content 96.7 percent, 10 mmol) was dissolved in 16.4 g of a formic acid water mixture (95:5) and the solution was stirred for 2 hours at 0° C. Then the mixture was concentrated by evaporation at 20° C./0.1 mbar. The residue (0.66 g) was washed with 1.5 ml of ethyl acetate and dried. The yield of product was 0.32 g, with a content (HPLC) of 94.1 percent, which corresponds to 35.8 percent of theory. The melting point of the product was 112° C. (decomposition).

What is claimed is:

1. A process for the production of squaric acid of formula:

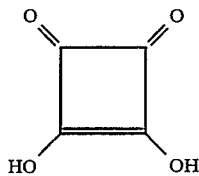

VII comprising halogenating a 1,3-cyclobutanedione-bisketal of formula I:

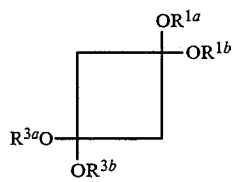

I wherein either $R^{1a}$, $R^{1b}$, $R^{3a}$ and $R^{3b}$ are the same and respectively each represents a linear or branched lower alkyl group, or respectively $R^{1a}$ and $R^{1b}$ as well as $R^{3a}$ and $R^{3b}$ together mean the same and with the ketal oxygen atoms and the intermediate carbon atom respectively form a five-membered or six-membered spiro-linked ring with the cyclobutane ring optionally substituted by one or more lower alkyl groups and then hydrolyzing said halogenated 1,3-cyclobutanedione-bisketal of formula I to squaric acid.

2. The process according to claim 1 wherein the halogenation is performed with elementary chlorine or bromine.

3. A process for the production and/or purification of 1,3-cyclobutanedione, comprising hydrolyzing a 1,3-cyclobutanedione-bisketal of formula I in the presence of an acid, said 1,3-cyclobutanedione-bisketal of formula I being:

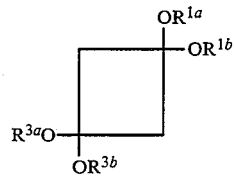

I wherein either $R^{1a}$, $R^{1b}$, $R^{3a}$ and $R^{3b}$ are the same and respectively each represents a linear or branched lower alkyl group, or respectively $R^{1a}$ and $R^{1b}$ as well as $R^{3a}$ and $R^{3b}$ together mean the same and with the ketal oxygen atoms and the intermediate carbon atom respectively form a five-membered or six-membered spiro-linked ring with the cyclobutane ring optionally substituted by one or more lower alkyl groups.

4. The process as claimed in claim 1 wherein the halogenation is performed in the presence of water.

5. The process as claimed in claim 1 wherein the halogen used in the halogenation is present in an amount of 2.5 to 4 mols per mol of 1,3-cyclobutanedione-bisketal.

6. The process as claimed in claim 1 wherein the halogenation is conducted in the presence of a protic or an aprotic solvent which is resistant to elementary halogen.

7. The process as claimed in claim 1 wherein the solvent is selected from the group consisting of lower aliphatic carboxylic acids, esters of lower aliphatic carboxylic acids, anhydrides of lower aliphatic carboxylic acids and halogenated alkanes.

8. The process as claimed in claim 1 wherein the halogenation is conducted at a temperature of 0° to 80° C.

9. The process as claimed in claim 1 wherein the hydrolysis is performed with water or an aqueous acid.

10. The process as claimed in claim 1 wherein the aqueous acid is an aqueous mineral acid, an aqueous strong carboxylic acid or an aqueous sulfonic acid.

11. The process as claimed in claim 1 wherein the hydrolysis is performed with aqueous sulfuric acid.

12. The process as claimed in claim 1 wherein the amount of water used is 2 or more mols per mol of the squaric acid produced.

13. The process as claimed in claim 1 wherein the hydrolysis performed at a temperature of 50° to 150° C.

* * * * *